United States Patent [19]

Degen et al.

[11] Patent Number: 4,693,985
[45] Date of Patent: Sep. 15, 1987

[54] METHODS OF CONCENTRATING LIGANDS AND ACTIVE MEMBRANES USED THEREFOR

[75] Inventors: Peter J. Degen, Huntington; Jerold Martin, Plainview; Judy Schriefer, Commack, all of N.Y.; Brenda Shirley, Athens, Ga.

[73] Assignee: Pall Corporation, Glen Cove, N.Y.

[21] Appl. No.: 642,899

[22] Filed: Aug. 21, 1984

[51] Int. Cl.[4] .................... B01D 15/08; B01D 39/00; G01N 33/545

[52] U.S. Cl. ................... 436/531; 210/198.2; 210/493.1; 210/500.38; 210/502.1; 210/635; 435/13; 435/180; 435/181; 436/532; 436/548; 436/824; 436/827; 436/828

[58] Field of Search .............. 436/531, 532, 548, 824, 436/827, 828; 435/180, 182, 181; 525/420.5; 210/198.2, 493.1, 500.38, 502.1, 635

[56] References Cited

U.S. PATENT DOCUMENTS

| 3,652,761 | 3/1972 | Westall . |
| 3,824,150 | 7/1974 | Lilly et al. . |
| 3,843,324 | 10/1974 | Edelman .................................. 435/2 |
| 4,035,146 | 7/1977 | Brenner et al. . |
| 4,229,537 | 10/1980 | Hodgins et al. . |
| 4,255,412 | 3/1981 | Albert .................................. 436/531 |
| 4,266,026 | 5/1981 | Bresldu .......................... 435/182 X |
| 4,357,311 | 11/1982 | Schutt . |
| 4,361,484 | 11/1982 | Larsson et al. . |
| 4,361,509 | 11/1982 | Zimmerman et al. . |
| 4,490,290 | 12/1984 | Gani et al. . |
| 4,549,011 | 10/1985 | Herzberg et al. . |
| 4,560,504 | 12/1985 | Arnold .......................... 260/112 B |
| 4,615,985 | 10/1986 | Deutsch et al. ..................... 436/531 |

FOREIGN PATENT DOCUMENTS

| 0061312 | 9/1982 | European Pat. Off. . |
| 0069869 | 1/1983 | European Pat. Off. . |
| 0090483 | 10/1983 | European Pat. Off. . |
| 2939443 | 4/1980 | Fed. Rep. of Germany . |
| 1333647 | 10/1973 | United Kingdom . |
| 1346631 | 2/1974 | United Kingdom . |
| 1519675 | 8/1978 | United Kingdom . |

OTHER PUBLICATIONS

U.S. patent application Ser. No. 459,956, filed Jan. 21, 1983 by Degen et al.
"Quantitative Removal of Hepatitis B Viral Antigens from Serum by a Monoclonal IgM Coupled to a Biocompatible Solid-Phase Support" by Marciniak et al, Proc. Natl. Acad. Sci. USA, 80, 3821-3825 (1983).

Primary Examiner—Sidney Marantz
Attorney, Agent, or Firm—Leydig, Voit & Mayer

[57] ABSTRACT

A chemically active membrane having a large surface area is provided in which a hydrophilic, microporous, skinless, polyamide membrane is chemically bound to a residue of an activating agent which is capable of reacting with a biologically active material.

The chemically active membrane, formed by reacting a hydrophilic, microporous, skinless, polyamide membrane with an activating agent may be used to prepare a biologically active membrane having a large surface area which comprises an acceptor molecule such as a monoclonal antibody, a polyclonal antibody, an antigenic substance, a glycoprotein, Protein A, a lectin, a carbohydrate, an enzyme substrate, a cofactor, an inhibitor, a hormone, an IgG class of immunoglobulin, a carrier protein, a receptor, heparin, a coagulation factor, or a histone covalently bound to the hydrophilic, microporous, skinless, polyamide membrane by reacting the chemically activate membrane with the acceptor molecule.

61 Claims, 2 Drawing Figures

METHODS OF CONCENTRATING LIGANDS AND ACTIVE MEMBRANES USED THEREFOR

TECHNICAL FIELD

The present invention relates to methods of immobilizing biologically active materials and compositions used therefor. More particularly, the present invention relates to a method for forming a chemically active membrane, to chemically active membranes capable of immobilizing biologically active materials, to a method for preparing biologically active membranes, to biologically active membranes in which a biologically active material is bound to a membrane, and to a method of binding a ligand to and releasing the ligand from such a biologically active membrane.

BACKGROUND ART

A variety of materials have been used for isolation and identification of biologically active substances, generally, and ligands particularly. As techniques have been developed for isolation of such biologically active substances, the ability to discriminate among the materials present in a mixture and selectively separate those desired has increased. One of the techniques which has been developed and refined to permit ever-increasing selectivity employs solid supports, especially particulate supports, on which a biologically active substance is ultimately bound and retained, either by a physical attraction, such as by adsorption, or by a chemical reaction. The significant interest in such a potent tool for immobilizing and either isolating and identifying biologically active substances or ligands or for use of such materials in subsequent procedures is at least partially attributable to the ease of manipulation of such solid supports or substrates and thereby the immobilized substances. The availability of such supports and procedures for immobilizing biological materials has stimulated research directed to improving and providing greater selectivity in techniques employed for separation or concentration of biologically active materials, such as affinity purification, particularly affinity chromatography, and the biospecific adsorbents used for such purposes, including solid supports, biologically active materials and, in some instances, activating or linking agents used to form a bond between a biologically active material and the solid support.

Those materials used as solid supports or carriers for binding biologically active materials have included most frequently polymers, usually of natural origin, containing hydroxyl groups in free or esterified form, such as agarose, cellulose, including cellulose esters such as cellulose nitrate, cellulose acetate, cellulose propionate, and the like, and acrylamide polymers and copolymers, such as polyacrylamide and acrylamide copolymer gels.

Many combinations of solid support and linking agent have been somewhat effective in immobilizing biologically active materials and specific compounds, either in removal of such materials from fluids, performing specific biological reactions or for use in immunoassays. Thus, particular choices of solid support and linking or activating compounds, when used to immobilize one member of an immune or biospecific complex such as in an antigen/antibody pair, hapten/antibody pair, apoprotein/cofactor pair, lectin/carbohydrate pair, or the like, have proven to be somewhat effective when the combination of solid support and the immobilized one member is used for binding an immune or biospecific ligand, that is, the second member of the biospecific or immune complex, to thereby form the immobilized complex.

The ability to immobilize a particular biologically active material, such as an antibody, particularly a monoclonal antibody, on a solid support provides an important tool in binding and qualitatively identifying and/or quantifying, or simply removing from a solution, the other member of an immune or biospecific complex, such as an antigen. However, the number of solid supports, linking agents or combinations of support and linking agent capable of immobilizing a wide variety of biologically active materials is limited.

Despite notable developments which have occurred in the technology related to immobilization of biologically active materials on solid supports, limitations in the techniques have frequently resulted from either the chemical or physical properties of the support materials employed.

Among the chemical shortcomings of materials used either as solid supports or as agents for coupling a biologically active material to the support have included:
 (a) weak chemical bonding,
 (b) strong chemical bonding, thereby inhibiting attempts to elute a desired material from the column,
 (c) the necessity to employ somewhat extreme conditions to effect reaction, such as high temperature and pH,
 (d) coupling or activating agents which are capable of reacting with only a limited number of chemical groups on either a solid support or a biologically active compound, and
 (e) solid supports which have only a limited number of chemical groups capable of reacting with coupling or activating agents.

Many of the solid supports currently available exhibit mechanical properties which limit their usefulness in affinity chromatography applications. Conventional affinity chromatography materials generally employ biologically active materials immobilized on solid beads which are packed into tubular columns. The use of compressible materials, such as those from which most beads are made, which materials are currently preferred, may limit the dimensions and capacity of the column due to compression of the beads under excessive hydrostatic pressure resulting in an increase in pressure drop through the column and a subsequent decrease in flow rate, as well as a decrease in bead life. The efficiency of such columns may be further limited since a decrease in the size of the beads to provide an increase in surface area and, thereby, an increase in the effectiveness or rate of removal of material from the olution passing through the column, may cause this increase in pressure drop and decrease in flow rate to become more pronounced. In those situations in which recovery of biological material is performed on a large scale using large volumes of solution, as on a commercial preparative scale, the shortcomings of such beads become magnified. Thus, column dimensions must be selected as a compromise between elongated columns providing satisfactory separation but lacking reasonable flow rates and those allowing adequate flow rates but recovering biological material of reduced purity.

Although support materials in the form of membranes have been developed which overcome many of the aforementioned problems, particularly some of the chemical problems, many of these materials are asymmetric or skinned membranes which either require somewhat elaborate apparatus for their use or a means to provide a substantial head of pressure in order to effect flow of ligand-containing solutions through the asymmetric membranes.

DISCLOSURE OF INVENTION

The present invention is directed to a method for immobilizing a wide range of biologically active substances or materials as acceptor molecules on active membranes, the active membranes used therefor and a method of preparing such membranes, and the biologically active membranes resulting from for immobilization of such acceptor molecules. The present invention also contemplates a method of selectively binding those substances capable of forming stable biospecific complexes with acceptor molecules, referred to herein as ligands, to the biologically active membranes and the use of this latter technique to remove ligands from a fluid, particularly a biological fluid.

The invention described herein is expected to have most widespread application as a method and a material for the separation and/or concentration of selected ligands, both wanted and unwanted, from fluids, particularly biological fluids, on both small and large scales. The ability of the biologically active membranes of the present invention to immobilize and bind a wide variety of biologically active compounds, specifically ligands to acceptor molecules, and to release such ligands and regenerate the biologically active membranes upon subsequent treatment provides thereby a method and composition, specifically a biologically active membrane, for isolating and purifying biologically active compounds which comprise the ligands. Thus, by appropriate choice of biologically active material which is immobilized as the acceptor molecule and source of similar biological material, which similar biological material is most frequently the counterpart or ligand of the immobilized biologically active material in a biospecific complex, the present invention permits the ligand to be obtained in quantity and high degree of purity. The biologically active membranes of the present invention, having the ability to remove ligands, such as antigens and haptens, from solutions also provide a method and material for purifying biological fluids, such as bodily fluids or constituent parts thereof, particularly blood, serum, plasma, and the like, by removal of the unwanted or selected ligands. Such purification or concentration procedures may be achieved, in many instances, by embodiments of the present invention adapted for use in affinity purification techniques, such as affinity chromatography, and to a membrane used therefor. The present invention is also expected to have application where the immobilization of biologically active compounds may be used as an assay tool, particularly in immunoassay procedures, for the quantitative and/or qualitative determination of minute quantities of a variety of biologically related substances present in or obtained from bodily fluids, such as blood, serum, plasma, urine, saliva, and the like. The present invention may be employed in various types of immunoassays, such as those where a particular label is employed, such as one indicating radioactivity, enzyme activity or an electromagnetic absorbing and/or emitting label, such as a fluorescent label.

One of the components used to form both the chemically active and biologically active membranes of the present invention is a hydrophilic, microporous, skinless, polyamide membrane. This imparts to the chemically active and biologically active membranes qualities which provide such membranes with advantages over known materials used for the same or similar purposes; namely, the membranes of the present invention are characterized by high porosities and surface areas and low pressure drops across the membranes. As a result of such properties, the membranes of the instant invention permit procedures to be performed more rapidly and efficiently.

The active or chemically active membranes of the present invention comprise an activating agent which, in many instances, also serves as a linking group, the activating agent being bound to a hydrophilic, microporous, skinless, polyamide membrane. The biologically active membranes of the present invention include membranes in which an acceptor molecule, generally in the form of a biologically active material, is bound to a hydrophilic, microporous, skinless, polyamide membrane either directly or through a linking group. As used herein, the term "biologically active material" may be broadly characterized as a substance of the type found in nature, generally a macromolecule, which is frequently a proteinaceous substance but, in some instances, may be a carbohydrate or other substance. The "acceptor molecule", which is a biologically active material, may generally be any material which, as a first member, is capable of binding a ligand as a second member. The second member, which may also be a material fitting the description of a biologically active material, as used herein, forms a biospecific complex with the first member (acceptor molecule). In most instances, the acceptor molecule is a proteinaceous material such as an immunoglobulin or antibody (either polyclonal or monoclonal), an antigenic substance, an apoprotein, a receptor, a glycoprotein or a lectin and, in some cases, a non-proteinaceous substance, such as a carbohydrate, a hormone or other type of naturally occurring substance.

The present invention also contemplates a method for preparing both chemically activated membranes and biologically active membranes made therefrom. The chemically activated membrane may be prepared by reacting an activating agent with a hydrophilic, microporous polyamide membrane, preferably a skinless polyamide membrane with controlled surface properties, to form a chemically activated membrane. The chemically activated membrane may then be treated with an acceptor molecule to form a biologically active membrane, which biologically active membrane, depending upon the nature of the material bound to the membrane, may be employed in binding a ligand to form a biospecific complex for use in separation or concentration procedures or, alternatively, in an immunoassay procedure.

The present invention also contemplates a method for immobilizing or binding a ligand. This method includes forming a chemically activated support or membrane by reacting a hydrophilic, microporous, preferably skinless, polyamide membrane with an activating agent to form a chemically activated membrane, which activated membrane is thereafter contacted with a biologically active material, i.e., acceptor molecule, to form a biologically active membrane. The biologically active membrane may then be exposed to a fluid, such as a biological liquid, containing a ligand to thereby bind the ligand. The ligand, which is the second member of a biospecific complex, may also be described as a biological material of the same or similar type as the acceptor molecule, such as a proteinaceous material or substance as, for example, an antigenic substance, antibody, glycoprotein, apoprotein or lectin.

BEST MODES FOR CARRYING OUT THE INVENTION

Figure 1:
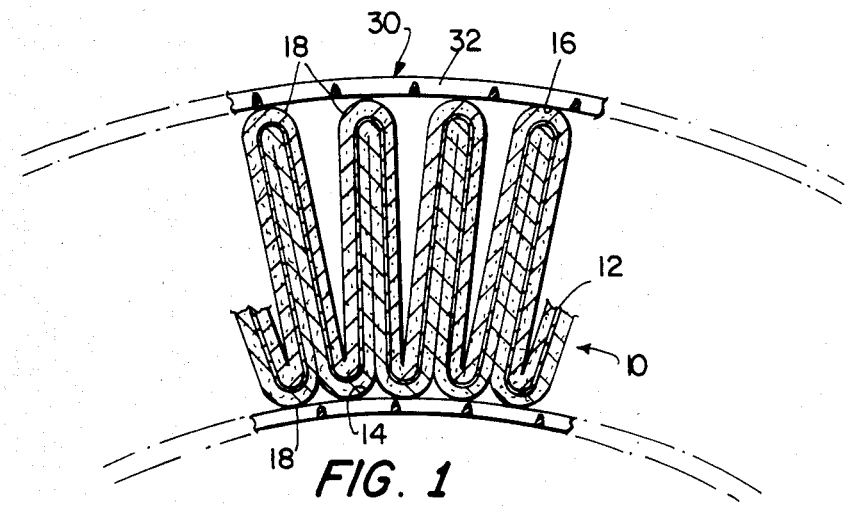
FIG. 1 is a partial sectional view of an embodiment of the present invention taken along line I—I of FIG. 2.

Polyamide Membranes:

The membranes of the present invention comprise hydrophilic, microporous, skinless, polyamide membranes. The polyamide is, preferably, a nylon of the type described in U.S. Pat. No. 4,340,479, which is incorporated herein by reference. As described therein, preferred nylons include polyhexamethylene adipamide, poly-$\epsilon$-caprolactam, polymethylene sebacamide, poly-7-aminoheptanoamide or polyhexamethylene azeleamide, with polyhexamethylene adipamide (nylon 66) being most preferred. Particularly preferred are skinless, substantially alcohol-insoluble, hydrophilic polyamide membranes. These membranes are also characterized as having a ratio of methylene $CH_2$: amide NHCO within a range of about 5:1 to about 7:1. A membrane material of this description which is particularly useful for the present invention is available from Pall Corporation under the trademark ULTIPOR N66.

It is believed that the novel properties of this preferred type of membrane result, at least in part, from concentrations on the membrane surface of amine and carboxylic end groups of the polyamide. Terms such as "surface" or "membrane surface", used in the singular or plural, are intended herein to include both external or outer surfaces, such as those which are exposed to view, as well as internal surfaces or those surfaces which define the pores of the membrane. That is, the membrane surface is that portion of the membrane which is capable of being contacted by a fluid, particularly a liquid. As distinguished from the "membrane surface area", the exposed planar dimensional area of the membrane material is herein referred to as the "membrane area".

Included among the preferred polyamide membranes are hydrophilic, microporous, skinless polyamide membranes with controlled surface properties of the type described in U.S. patent application Ser. No. 850,061, filed Apr. 7, 1986, which is a Continuation of U.S. patent application Ser. No. 459,956, filed Jan. 21, 1983, now abandoned which is a Continuation-In-Part Application of U.S. patent application Ser. No. 346,118, filed Feb. 5, 1982, now abandoned and in U.S. patent application Ser. No. 848,911, filed Apr. 7, 1986, which is a Continuation of U.S. patent application Ser. No. 460,019, filed Jan. 21, 1983, now abandoned which is a Continuaion-In-Part Application of U.S. patent application Ser. No. 346,119, filed Feb. 5, 1982 now abandonded. All of the aforementioned U.S. patent applications are specifically incorporated herein by reference. These hydrophilic, microporous, substantially alcohol-insoluble polyamide membranes with controlled surface properties are formed by cocasting an alcohol-insoluble polyamide resin of the type described above, i.e., having a ratio of methylene $CH_2$:amide NHCO groups within the range of from about 5:1 to about 7:1, with a water-soluble, membrane-surface-modifying polymer having functional polar groups. Like the preferred hydrophilic, microporous nylon membranes which do not have controlled surface-modifying polar groups present, as described above, the polyamide membranes of the present invention having controlled surface properties are also skinless. That is, they are characterized by through pores extending from surface to surface which are of substantially uniform size and shape. If desired, however, tapered through pores, i.e., pores which are larger at one surface of the sheet, narrowing as they approach the opposite surface of the sheet, may be used.

The surface-modifying polymers used to prepare the polyamide membranes with controlled surface properties, useful in the present invention, comprise polymers which contain substantial proportions of nucleophilic, chemically functional groups, such as hydroxyl, carboxyl, amine and imine groups. As a result, the membranes include, at their surfaces, high concentrations of functional groups such as hydroxyl, carboxyl, amine, or a combination of any of the above groups which do not react with one another. These polyamide membranes having controlled surface properties have higher concentrations of carboxyl or amine groups at their surfaces than the preferred microporous, hydrophilic, skinless polyamide membranes described above, which do not have controlled surface properties, i.e., those which are formed from the preferred polyamide resin but are not cocast with a surface-modifying polymer.

Particularly useful as the membrane material of the present invention is a hydrophilic, microporous, substantially alcohol-insoluble polyamide membrane formed from hexamethylene adipamide having the aforementioned methylene $CH_2$:amide NHCO group ratio which has controlled surface properties resulting from inclusion of a high concentration of carboxyl moieties. The inclusion of surface carboxyl moieties results from cocasting the nylon with a copolymer containing an abundance of carboxyl groups. A membrane material of this description which is particularly useful for the present invention is available from Pall Corporation under the trademark CARBOXYDYNE.

Other materials which are particularly useful in the present invention include membranes employing the aforementioned hydrophilic, microporous, skinless, substantially alcohol-insoluble hexamethylene adipamide having controlled surface properties in which the surface has been modified with amine functional groups by cocasting the nylon with a polymer containing an abundance of primary and secondary amine groups. Particularly preferred is a material known as AMINODYNE ™, available from Pall Corporation. Membranes formed from the above described hydrophilic, microporous, skinless polyhexamethylene adipamide which contain hydroxyl-modified surfaces are also useful in the present invention, and another preferred material is known as HYDROXYDYNE ™ which is available from Pall Corporation. This material is prepared by cocasting the nylon resin with a polymer containing an abundance of hydroxyl groups.

In preparing the hydrophilic, microporous membranes of the present invention, both those modified to have controlled surface properties and unmodified, a solution of the casting resin, including a surfacemodifying polymer when the membrane is to be so modified, is cast on a supporting surface, as described in U.S. Pat. No. 4,340,479. In most instances, the final membrane product is intended to be an internally supported membrane. That is, the supporting surface on which the resin is cast becomes an integral part of the final membrane as a permanent supporting layer or substrate. To impart permanency to the structure, the substrate should, therefore, be one which readily adheres to the casting resin solution and solidified membrane and be of a porous material. The preferred substrates for use in the present invention are those having pores larger than the membranes which they support. Although the membrane may be supported on one surface thereof by the substrate, the embodiment which is particularly preferred is one in which the material of the substrate is embedded in the membrane. Examples of suitable materials to use as substrates in the membranes of the present invention, as indicated in U.S. Pat. No. 4,340,479, include nonwoven or woven fibrous materials, such as nonwoven mats and batts, and woven textiles and cloth and, additionally, netting. Appropriate materials include polyolefins, such as polypropylene or polyethylene, polyesters, polyimides, aromatic polyamides, cellulose, regenerated cellulose, cellulose derivatives, such as esters and ethers, and the like.

The pore diameter of the membranes, either unsupported or supported, is suitably within the range of about 0.1 to about 1.2 microns. The preferred range of pore diameters is about 0.1 to about 0.65 microns.

Activating Agent

To provide a stable link or bond between a biologically active material, or acceptor molecule. and the membranes of the present invention, an "activating agent" is employed. A stable "activated membrane", which is the term applied herein along with "chemically activated membrane", or like terms, to the product formed by the reaction of the membrane and activating agent, allows the biologically active material to be immobilized or bound to the membrane by a covalent bond such that bleeding or leaching is obviated. Suitable activating agents comprise substances which include at least one functional group capable of reacting with reactive moieties on the membrane at the surface of the membrane to form a membrane having functional groups at its surface which are chemically reactive with biologically active materials.

Thus, some activating agents, of which trichloro-s-triazine (T-s-T) is representative, react with and become bound to the membrane by means of a first functional group in the activating agent to form an activated membrane. The activating agent T-s-T contains three reactive chlorine atoms, each capable of being displaced by a nucleophilic group either at the surface of the membrane or on a biologically active material. With activating agents of this type, the first functional group or atom of the activating agent reacts with reactive moieties at the surface of the membrane, thereby leaving a radical or residue of the activating agent bound to the membrane. In the case of T-s-T activated membranes, this s-triazine moiety still includes reactive chlorine atoms bound to each s-triazine radical or residue, which residue is covalently bound to the membrane. Each of these s-triazine bound chlorine atoms is capable of reacting with a biologically active material, or acceptor molecule, such that the latter becomes covalently bound to the membrane through the s-triazine residue. Activating agents of this type thus serve to activate the membrane in a first reaction and function as a linking agent by coupling a biologically active material to the membrane through a residue of the activating agent in a second reaction.

Other types of activating agents, of which carbodiimides are representative, also become bound and thereby activate the membrane. However, the activated product of this reaction includes a functional group which, if mechanisms proposed in the literature are correct, in the presence of a biologically active material results in loss or displacement of the residue of the carbodiimide and results instead in direct binding of the biologically active material to the membrane at the site formerly occupied by the residue of the carbodiimide.

Suitable materials to be used as the activating agent in the present invention are any of the materials generally known and used in the art for the same or similar purposes. Examples of preferred materials for use in the present invention as activating agents include, but are not limited to, carbodiimides, such as N, N'-dicyclohexylcarbodiimide (DCC) and 1-ethyl-3-(3-dimethylaminopropyl) carbodiimide; acid chlorides of organic polybasic acids, such as adipoyl chloride, terephthaloyl chloride, benzenedisulfonyl chloride and trichloro-s-triazine (T-s-T); cyanogen bromide; chloroacetic acid; dialdehydes, such as glutardialdehyde; diazobenzidine compounds, such as diazobenzidine, diazobenzidine-3,3'-diansidine and bisdiazobenzidine-2,2'-disulfonic acid; and polyfunctional isocyanates and thiocyanates, such as hexamethylene diisocyanate, toluene-2,4-diisothiocyanate, 3-methoxydiphenylmethane-4,4'-diisocyanate and toluene-2-isocyanate-4-isothiocyanate and diphenyl-4,4'-diisothiocyanate-2,2'-disulfonic acid. Particularly preferred are T-s-T and N, N'-dicyclohexylcarbodiimide. The use of T-s-T for certain applications as a linking agent is described in detail in U.S. Pat. No. 4,229,537.

Activated Membrane

Reaction of an activating agent with the hydrophilic, microporous membranes described above results in the formation of activated or chemically activated membranes, that is, membranes which contain groups or moieties active toward or capable of reacting with and immobilizing biochemical or biologically active materials on the membranes, which biologically active materials are acceptor molecules, generally in the form of macromolecules and most frequently proteinaceous macromolecules.

The particular procedure employed in forming the activated membrane will depend, in large part, on the choice of the activating agent to be employed. The activating agents suitable for use in the present invention are discussed in the immediately preceding section and particular procedures for their use are described adequately in the scientific literature. Generally, to prepare the activated membranes of the present invention, the polyamide membrane is placed in a suitable container in contact with a solution of the activating agent selected and an appropriate solvent suitable to dissolve the activating or linking agent and any other reagents required for the reaction occurring between functional groups on the surface of the membrane material and the activating agent.

For the formation of a T-s-T activated membrane, an organic base is included in the T-s-T "activation" or reaction solution. The membrane may be exposed to both the base and the T-s-T simultaneously or, preferably, the membrane is exposed to a solution of base first and then to the T-s-T. The membrane is preferably exposed to sufficient base and T-s-T to react with all of the functional groups available at the surface of the membrane, including the pores of the membrane. Generally, concentrations of about 0.1 molar to the limit of solubility in the particular solvent used for both the activating agent and the base provides satisfactory results. It is preferred that concentrations of each be about 0.1 molar to about 0.4 molar and that the base and activating agent be present in equimolar amounts. The support membrane is maintained submersed in the reaction solution or, alternatively and preferably, the reaction solution is passed through the membrane, generally at ambient temperature, for a period sufficient to effect substantial reaction between the activating agent and the functional groups on the surface of the membrane. The reaction period is generally about five minutes to about two hours and preferably, when the submersion technique is used, is about ten minutes to about one hour. It is also preferred, when the submersion technique is employed, that agitation be employed to assure adequate contact during the activation step between the reaction solution and the membrane material. The reaction solution is then decanted from the immersed membrane, which may be further washed to remove unreacted reagents. The preferred wash medium is generally the liquid which is used as the solvent or medium for the reaction solution or, alternatively, may be water or a buffer solution. Generally, the activated membranes are thereafter dried and may then be used to form the biologically activated supports described below.

When T-s-T is used as the activating agent, solvents suitable for use in the activation reaction are those capable of dissolving both the organic base and T-s-T, either as separate solutions or as a combined solution, and include methylene chloride, dioxane, tetrahydrofuran, acetone, or the like. Particularly preferred is methylene chloride because of high volatility which allows, therefore, its facile removal, and, additionally, because of its low flammability and relatively low toxicity.

Organic bases suitable for use are preferably tertiary amines, including diisopropylethylamine, triethylamine, diisopropylmethylamine, dimethylaniline, and pyridine. Particularly preferred as the organic base is triethylamine because of its availability and low cost.

When a carbodiimide, such as N, N'-dicyclohexylcarbodiimide (DCC), is used as the activating agent, the membrane is exposed to a solution of the carbodiimide in a suitable solvent. Employing procedures similar to those used with T-s-T or like activating agents, activation with carbodiimide or similar activating agents may be effected either with an immersion procedure or, preferably, by a "flow-through" procedure in which a solution of the activating agent is supplied from a reservoir by means of inert tubing and a supply means, such as a pump, to the membrane, which is held in a suitable holder. Preferably, the membrane should be exposed to sufficient carbodiimide to react with all of the functional groups available at the membrane surface. This generally corresponds to a concentration between about 0.1 molar and the limit of solubility in the solvent used, most preferably between about 0.1 and about 0.4 molar. The reaction period is commonly from about two minutes to about two hours, preferably from about five minutes to about one hour. It is preferred that agitation be employed to assure adequate contact during the activation step between the reaction solution and the membrane material when an immersion procedure is used in which the membrane material is placed in the solution of activating agent. The activating solution is then decanted from the immersed membrane and with either procedure the membrane is preferably washed successively to remove unreacted reagents. The preferred wash medium is generally the liquid which is used as the solvent or medium for the reaction solution or, alternatively, may be water or a buffer solution. The activated membranes are thereafter dried and may then be used to form the biologically activated supports described below.

When a carbodiimide such as DCC is used as an activating agent, solvents suitable for use in the activation reaction include methylene chloride, acetonitrile, pyridine, ether, dimethylsulfoxide, and tetrahydrofuran. Particularly preferred as the solvent is methylene chloride because of its high volatility, low flammability, and relatively low toxicity.

Biologically Active Membranes

The biologically active membranes of the present invention are formed by reacting the hydrophilic, microporous, skinless, activating agent-bound polyamide membrane, that is, the chemically activated membrane, with an acceptor molecule, or biologically active substance, to immobilize the latter on the microporous membrane surface. Immobilization results from covalent bonds formed either (a) between one or more of the remaining functional groups of the residue of the activating agent on the membrane surface and a functional group of the acceptor molecule, or (b) directly between a functional group on the surface of the membrane and a functional group of the biologically active material. The type of bond formed is a function of the type of activating agent employed, i.e., (a) one participating in the bond formed, that is, a linking group, or (b) one displaced in bond formation, respectively.

The terms "biologically active substance" "biologically active material", and also "biologically active membrane", or like terms, as used herein, refer to any substance which functions in the present invention as either an acceptor molecule or a ligand and which is capable of forming a biospecific complex, such as an immune complex, with another material. The term "biospecific complex", as used herein, means a complex formed between biologically active materials specific to one another, such as between an acceptor molecule and a ligand. Thus, a biologically active substance, for instance, an antibody, functioning as an acceptor molecule, may form a biospecific complex with another biologically active substance, termed herein a ligand, such as an antigen, to form a biospecific complex which, in the instant example, may also be termed an immune complex. The same antibody (biologically active substance), when bound to a membrane forms a biologically active membrane, which membrane now functions as an acceptor molecule which is capable of reacting with the same antigen (ligand) to form a biospecific complex. It should be noted that, in most instances, either member of a biospecific complex may be selected to serve as the acceptor molecule while the other member functions as a ligand.

The substances which form at least one member of the biospecific complexes of the present invention are frequently, but not always, macromolecules and include, most frequently, proteins. The type of substances which may serve as the biologically active acceptor molecules and those substances which function as the corresponding ligands in the biospecific complexes according to the present invention are listed in Table 1.

TABLE 1

| Biospecific Complexes | |
|---|---|
| Acceptor Molecule | Ligand |
| Polyclonal Antibody | Antigenic Substance |
| Monoclonal Antibody | Antigenic Substance |
| Antigenic Substance | Polyclonal Antibody |
| Antigenic Substance | Monoclonal Antibody |
| Glycoprotein | Lectin |
| Protein A | IgG Class Immunoglobulin |
| Lectin | Carbohydrate |
| Lectin | Glycoprotein |
| Carbohydrate | Lectin |
| Enzyme Substrate | Enzyme |
| Co-factor | Enzyme |
| Inhibitor | Enzyme |
| Hormone | Carrier Protein |
| Hormone | Receptor |
| Carrier Protein | Hormone |
| Receptor | Hormone |
| Heparin | Coagulation Factor |
| Coagulation Factor | Heparin |
| Histone | Nucleic Acid |
| Histone | Polynucleotide |

"Antigenic substances", as used herein, include antigens and haptens. In some instances the biologically active substance serving either as an acceptor molecule or ligand may also include polypeptides, albumins, globulins and amino acids.

To form the biologically active membrane of the present invention, the chemically activated membrane is contacted with an aqueous solution containing about 0.005 to about 10 mg/ml, preferably about 0.05 to about 0.5 mg/ml, of the biologically active material, i.e., acceptor molecule. These solutions are generally maintained at a physiologically compatible pH of about 7 to about 7.4 with a buffer, such as a phosphate buffered saline solution (PBS). The chemically activated membrane is exposed to a sufficient volume of the solution containing the biologically active material to immobilize about 30 to about 300 micrograms of the biologically active material per $cm^2$ membrane area. Contact of the solution of biologically active material with the activated membrane may be effected either by immersion of the membrane in the solution or by passing the solution through the membrane. When the former technique is employed, the membrane and solution are gently agitated for a period of time sufficient for substantially complete reaction, generally at least two hours. When the latter procedure is used, a solution of the acceptor molecule is supplied from a reservoir by means of inert tubing and a supply means such as a pump to the membrane, which is held in a suitable holder. In most situations, a single pass of the solution through the membrane is sufficient to immobilize the biologically active material within the pores and on the external pores of the membrane. The solution of the acceptor molecule is maintained at a temperature for most materials at about 0 to about 37 degrees, preferably at a temperature of about 4 degrees C. to and including ambient temperature. Thereafter, when employing the immersion technique, excess biologically active material is removed by decantation, and the portions of biologically active membrane are washed several times in water or a suitable buffer solution, such as a phosphate buffered saline solution, to remove residual unreacted biologically active material.

As indicated in Example 9 below, by virtue of the covalent bonds formed between an acceptor molecule and the surface of the membrane, either directly or through a linking group, the acceptor molecule is bound more firmly by an activated membrane than by a membrane which has not been activated by treatment with a suitable activating agent. Thus, the biologically active membranes prepared according to the present invention tend to be quite stable and demonstrate little loss of the biologically active material over extended periods of time under a variety of conditions.

The use to which the biologically active membrane is to be put strongly influences the choice of biologically active material to be immobilized or bound to the membrane. That is, the ligand or second member of the biospecific complex which is to be removed from the fluid passing through the biologically active membrane determines the type of acceptor molecule or first member of the biospecific complex to be bound to the active support. Thus, the possible antigen/antibody complexes, hapten/antibody complexes, apoprotein/cofactor complexes, lectin/carbohydrate, lectin/glycoprotein complexes or, generally, acceptor molecule/ligand biospecific complexes, that may be formed by the ligand sought to be removed or bound limits the choice of biological material which may be immobilized on the membrane. In most instances the choice tends to be rather restricted and specific, such as a specific antigen or antibody, while in others, less specificity exists and, as a result, a greater number of biospecific complexes may be formed with a particular biologically active material or ligand. For example, certain proteinaceous substances, such as Protein A, may be employed either as the biologically active material or acceptor molecule immobilized by the active membrane to form the biologically active membrane or may be removed from a solution as a ligand bound to the biologically active membrane. A material such as Protein A, therefore, may be used advantageously as the acceptor molecule in a biologically active membrane according to the present invention in affinity chromatography or in a similar application in order to remove mammalian immunoglobulins from different sources, such as human, rabbit, or mouse antibodies (IgGs) from bodily fluids, such as serum, or for isolation of some IgG-type immune complexes.

Binding A Ligand Specific To The Acceptor Molecule Material Immobilized On Biologically Active Membrane:

The biospecific adsorption or attachment of a ligand, such as an antigen, hapten, antibody or the like, to the biologically active membrane may be accomplished by passing a solution of an appropriate ligand through the biologically active membrane at a temperature of from about 0 to about 37 degrees C., preferably at a temperature of about 4 degrees C. to about ambient temperature. The ligand-containing solution is preferably buffered with a buffer suitable for maintaining the solution at a physiologically compatible pH of about 7.0 to about 7.4. A phosphate buffered saline (PBS) solution may be employed.

Prior to contacting the biologically active membrane with ligand-containing solution, the membrane is preferably treated by passing therethrough a buffer solution of the same pH as the solution of ligand and maintained at a temperature within the range set forth above for the ligand-containing solution.

If the ligand, such as an antigen, to be attached to the biologically active membrane is in a solution which additionally contains non-specific proteins, that is, proteins not capable of forming a biospecific complex with the biologically active membrane, the presence of such non-specific proteins does not generally create difficulties in isolating the ligand. To the contrary, in many instances such non-specific proteins serve to stabilize the ligand (specific protein) molecules. After treatment of the biologically active membrane with the ligand-containing solution, residual ligand, i.e., ligand which has not formed biospecific complexes with immobilized biologically active material, non-specific proteins and other solutes may be removed by washing with aliquots of buffer solution.

In those instances where the fluid in which the ligand is present, such as a human bodily fluid, as, for example, serum or plasma, is being sought in pure form, purification may be effected to the desired degree of purity by removal of the ligand, such as a serum or plasma protein or antigen, from the fluid, usually by a single pass through the membrane. In some instances, however, several passes may be required to attain the level of purity sought.

Where immunoassays are to be performed by employing a labeled material, such as a radioactive label, fluorescent label or enzyme label, the appropriately labeled ligand may be added to the ligand-containing solution being assayed in amounts suitable for detection.

Recovery Of Bound Ligands

Once bound to the biologically active membranes of the present invention by formation of a biospecific complex therewith, a ligand may be recovered in high purity and concentration and the biologically active membrane regenerated by extraction or elution of the membrane material with an appropriate extractant or eluent. Due to the advantages associated with the high porosity and low resistance to flow of the hydrophilic, microporous, skinless membranes of the present invention, elution is the preferred method of ligand recovery. Alternatively, extraction may be accomplished by immersing the membrane in a solution of the extractant.

The same material may generally be employed either as an eluent or an extractant. Materials suitable for use either as eluents or extractants are substances which are capable of disrupting the bonds formed between biologically active material or acceptor molecules and ligands of the biospecific complexes without irreversibly altering or inactivating either component of the biospecific complex. Particularly with proteinaceous materials, suitable substances are those which cause conformational changes in the members of the complex sufficient to disrupt a biospecific complex. Such conformational changes frequently result from breaking of hydrogen bonds or other disturbances of secondary and tertiary structures. Solutions of suitable extracting or eluting agents may be characterized, in most instances, although not exclusively, by low pH or high concentrations of chaotropic ions. Examples of preferred extractants or eluents, in the form of aqueous solutions, include urea or guanidine, about 4 to about 8 M, having a pH of about 7 to about 7.4; glycine.HCl, having a pH of about 2 to about 4; HCl of about 0.02 M and NaCl having a concentration of about 0.15 M; about 0.03 M sodium citrate having a pH of about 2.6; about 0.03 M sodium thiocyanate having a pH of about 2.6; and about 2.6 M NaI having a pH of about 9.0. The foregoing concentrations and pH values provided for the aqueous solutions of the preferred eluents are believed to provide the optimum conditions in most situations. However, conditions should be optimized for individual elutions. In some instances, for example, where it is desired to recover an antigen or antibody with minimal denaturation, it may be preferred to employ a pH closer to neutrality or a physiological pH value.

Affinity Chromatography Structure

The biologically active membranes of the present invention may be used most conveniently in the form of corrugated membranes, which membranes are also arranged, preferably, in a cylindrical configuration. Such structures are particularly preferred in applications to affinity chromatography. As noted earlier, most materials currently used as supports for affinity chromatography take the form of compressible beads which limits their efficiency in such applications because of large pressure drops and the consequent decrease in flow rates resulting from such compression.

The use of the biologically active membranes of the present invention, particularly in the aforementioned corrugated cylindrical configurations, although capable of being used for the same or similar purposes as conventional affinity chromatography columns, functions in a manner more similar to a cylindrical filter element than a chromatography unit. That is, the element is arranged so that the biologically active material-containing solution passes from one surface of the membrane to the other surface thereof through the pores of the filter, in much the same manner as a particulate-containing solution which forms the filtrate in a conventional filtration, whereas a solution passing through a conventional chromatography column circulates around the support particles in the column. It has been found that the biologically active membranes of the present invention, particularly as elements in the corrugated cylindrical configuration described herein, provide a marked increase in efficiency over conventional columns used in affinity chromatography. Such efficiency results from a number of different features. The microporous nature and high void volumes of the hydrophilic, microporous membranes of the present invention provide an extremely large surface area to which the biologically active material is bound. For example, a membrane with a pore diameter of 0.1 micron and a thickness of about 5 mils has a total surface area of 130 $m^2/ft^2$ of surface area. A membrane with a pore diameter of 0.2 micron and a thickness of about 5.5 to about 6 mils and a membrane area of about 9 square feet has a total available membrane surface area of 650 $m^2$. The membranes used in the present invention generally have pore diameters of slightly less than 0.1 micron to larger than 0.45 micron which provide BET surface areas of slightly greater than about 24 $m^2$/gram of membrane to less than 8 $m^2$/gram of membrane. As a result, an extremely large number of sites exist in the path taken by the ligand-containing solution over and through the membrane for interaction between a ligand in solution and a bound biologically active substance. Furthermore, the corrugated cylindrical structure of the present invention also provides a large membrane area per unit of volume. For instance, a corrugated structure in which a pleated membrane having a length of approximately 10 inches and an outer diameter of about 2.5 inches with approximately one-half inch of pleat depth provides a membrane area on the order of about 5 to 9 square feet. The membrane area and concommitant efficiency of such a structure may be increased by providing a plurality of concentric corrugated membranes. Thus, on a volume basis, the effectiveness of removal of ligands from solutions flowing through corrugated structures employing biologically active membranes according to the present invention far exceeds conventional bead-immobilized, biologically active supports employed in affinity chromatography.

Figure 2:
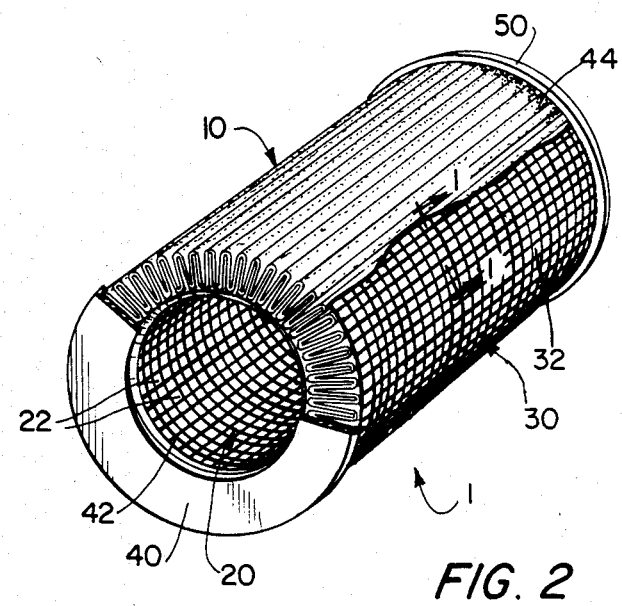
FIG. 2 is a perspective cutaway view of an embodiment of the present invention.

The preferred structure 1 for such corrugated membrane devices, illustrated in FIGS. 1 and 2, includes the preferred membrane element 10 formed from a membrane material 12 which is preferably a supported membrane material, i.e., a membrane material in which a substrate is embedded, as described previously. The membrane material is enclosed between coarser protective layers 14 and 16. The membrane element is arranged in the form of a pleated cylinder, having corrugations 18, surrounding a cylindrical or tubular perforated core 20 having perforations 22 therein. The corrugated tubular membrane element 10 is placed within a cylindrical or tubular outer cage 30 having perforations 32 therein. End caps 40 and 50 are sealed to the open ends of the cylindrical core 20, membrane element 10 and outer cage 30 so as to close off and form a leak-tight seal between each of the aforementioned substantially cylindrically configured substructures. Any method known to those skilled in the art may be used to secure the end caps to the membrane element, core and cage. Preferred techniques include those taught by U.S. Pat. No. 3,457,339, incorporated herein by reference. A hole 42 is placed in one of the end caps 40 to provide communication to the interior of the cylindrical core.

In operation, the cylindrical corrugated structure of the present invention may be placed within a suitable housing such that a ligand-containing solution passes sequentially through outer cage 30, membrane element 10 and core 20 such that the ligand-reduced or ligand-free solution, after passing into the interior portion of the core through apertures 22, exits from structure 1 through hole 42. It is possible, and in some instances it may be preferred, to have the ligand-containing solution flow in a direction opposite to that described above such that the solution enters structure 1 through hole 42 and exits from the perforations 32 in the outer cage 30. Materials suitable for use in this structure have been identified previously for the membrane material, substrate and coarser protective layers. With respect to the core, cage and end caps, any plastic which is inert toward biologically active materials and substances commonly accompanying such materials in biological fluids is suitable for use in forming these component parts. Such plastics as polyolefins, for instance polyethylene and polypropylene, polyesters, as well as halogenated polymers, are quite suitable. The coarse protective layers may be formed from the same or similar materials and polypropylene is preferred.

The protective layers 14 and 16 provide rigidity to the membrane element and symmetrical spacing of the pleats thereof. The upstream support additionally serves to retain particulate material which may accompany the ligand-containing solution. The downstream protective layer 14 additonally serves to assist in drainage.

The type of corrugated structure described above and illustrated in the figures may also contain one or more additional corrugated, tubular membrane elements which are arranged concentrically with respect to membrane element 10.

EXAMPLES

While the invention is susceptible to various modifications and alternative forms, certain specific embodiments thereof are described in the general methods and examples set forth below. It should be understood, however, that these examples are not intended to limit the invention to the particular forms disclosed but, on the contrary, the intention is to cover all modifications, equivalents and alternatives falling within the scope of the invention.

All membranes used in the examples which follow are supported membranes, i.e., they incorporate the substrate on which the membrane material was cast.

EXAMPLE 1. General Method of Preparing Trichloro-s-Triazine Activated Membranes (a) Flow Through Procedure Trichloro-s-triazine (T-s-T) activated membranes were prepared as follows. Membrane discs of the desired size were cut from sheets of hydrophilic, microporous, skinless, substantially alcohol-insoluble, polyamide membrane material having a nonwoven polyester support embedded therein. The membrane discs were each placed in separate syringe-type filter holders and, according to the preferred procedure, were first prereacted by passing through them, using a peristaltic pump, an aliquot (3.0 ml/cm$^2$ of membrane area) of a solution composed of 4.3 ml triethylamine dissolved in 65 ml of methylene chloride at a flow rate of 0.3 ml/minute/cm$^2$ membrane area. An aliquot (3.0 ml/cm$^2$ of membrane area) of a T-s-T solution composed of 4.3 ml triethylamine and 2.0 g T-s-T in 65 ml methylene chloride was then passed through and recirculated through each membrane at a flow rate of 0.3 ml/minute/cm$^2$ membrane area for a period of one hour at ambient temperature. Following the reaction of polyamide membranes with T-s-T, unreacted T-s-T was removed by passing an aliquot (3.0 ml/cm$^2$ of membrane area) of methylene chloride through each membrane disc. The T-s-T activated membrane discs were thereafter removed from the filter holders, blotted dry on filter paper and air dried for about 15 minutes. The membranes were subsequently stored in a desiccator under vacuum at ambient temperature until required for use.

(b) Immersion Procedure:

T-s-T activated membranes were prepared by placing discs of polyamide membrane of the type described immediately above in a solution containing 4.3 ml triethylamine in 65 ml of methylene chloride contained in a 250 ml Erlenmeyer flask. The discs were submersed in the flask below the level of solution and were allowed, in a preferred procedure, to prereact with the triethylamine/methylene chloride solution for a 5 minute period at ambient temperature with continuous agitation. To the flask were then added 2 grams of T-s-T. Polyamide discs were reacted with T-s-T for 1 hour at ambient temperature. Thereafter, the T-s-T solution was decanted and the membrane discs washed 5 times with 50 ml aliquots of triethylamine/methylene chloride solution for 5 minutes per wash to remove unreacted T-s-T. The chemically activated membranes were blotted dry on filter paper, air dried for 15 minutes, and stored under vacuum in a desiccator at ambient temperature until required for use.

EXAMPLE 2, Preparation Of A Trichloro-s-Triazine Activated Hydrophilic Nylon 66 Membrane A T-s-T activated membrane was prepared according to the general method described in Example 1(b) employing as the polyamide membrane material described therein a nylon 66 polyamide membrane. This material, obtained from Pall Corporation under the trademark ULTIPOR $N_{66}$, had a pore diameter of 0.2 micron.

EXAMPLE 3, Preparation of A Trichloro-s-Triazine Activated Nylon 66 Membrane Having Surface-Modified Amine Functional Groups A T-s-T activated membrane was prepared according to the general method discussed in Example 1(b) from a hydrophilic, microporous, skinless, nylon 66 membrane material having controlled surface properties. The membrane, which had its surface modified with amine functional groups, was obtained by cocasting nylon 66 with a polymer containing an abundance of primary and secondary amine groups. This material was obtained from Pall Corporation under the trademark AMINODYNE. This membrane had a pore diameter of 0.1 micron.

EXAMPLE 4, Preparation Of A Trichloro-s-Triazine Activated Membrane Having Controlled Surface Properties Characterized By Carboxyl Functional Groups

(a) Flow Through Procedure

A hydrophilic, microporous, skinless, nylon 66 membrane having controlled surface properties characterized by carboxyl functional groups was prepared by cocasting nylon 66 with a polymer containing an abundance of carboxyl groups. This membrane material is available from Pall Corporation under the trademark CARBOXYDYNE. This membrane was activated with T-s-T solution in the manner described in the general method of Example 1(a), absent the triethylamine/methylene chloride pre-reaction step. Specifically, a 10 ml aliquot of a solution taken from a stock solution containing 4.3 ml triethylamine and 2.0 g of T-s-T in 65 ml methylene chloride was passed through a 25 mm diameter membrane disc of the above material at a flow rate of 0.3 ml/minute/$cm^2$ membrane area. Unreacted T-s-T was removed by flushing the membrane disc with 10 ml of methylene chloride at a flow rate of 0.3 ml/minute/$cm^2$ membrane area.

(b) Immersion Procedure

T-s-T activated membranes were prepared as described in the general method of Example 1(b) employing membranes having the same carboxyl functional group modified surfaces as those used in Example 4(a). Membranes of this material having pore diameters of either 0.1 micron or 0.2 micron were activated.

EXAMPLE 5, General Method of preparing N, N'-Dicyclohexylcarbodiimide Activated Membranes

(a) Flow Through Procedure

Hydrophilic, microporous, skinless, substantially alcohol-insoluble, polyamide membrane discs internally supported with a nonwoven polyester substrate material embedded therein were chemically activated with N, N'-dicyclohexylcarbodiimide (DCC) by the preferred method described below. A 10 percent (w/v) solution of DCC in methylene chloride (3 to 7 ml/$cm^2$ membrane surface area) was transferred from a reservoir through a length of tubing by means of a peristaltic pump to each membrane disc secured in a 25 mm diameter holder. The DCC solution was recirculated at a flow rate of 7.2 ml/minute/$cm^2$ membrane area through the membrane discs for a period of about 1 hour at ambient temperature. Each membrane disc was then flushed with 3 to 7 ml/$cm^2$ membrane area of methylene chloride. The DCC activated membranes were thereafter removed from the filter holders, blotted dry on filter paper, and air dried for 15 minutes. The membranes were stored in a desiccator under vacuum at ambient temperature until required for use.

(b) Immersion Procedure

Membrane discs as described immediately above were alternately activated with DCC by placing discs of the membrane material into a 250 ml Erlenmeyer flask containing a sufficient volume to cover the membrane discs of a 10 percent (w/v) solution of DCC in methylene chloride. Reaction was continued for a period of 5 minutes to 2 hours, as specified below, at ambient temperature with continuous agitation. Thereafter, the DCC solution was decanted and the membranes were washed with 5 successive 50 ml portions of methylene chloride for 5 minutes per wash. The DCC activated membranes were blotted with filter paper, air dried for about 15 minutes and stored under vacuum in a desiccator at ambient temperature until required for use.

EXAMPLE 6, Preparation of N, N'-Dicyclohexylcarbodiimide Activated Nylon 66 Membranes Having Controlled Surface Properties Characterized by Carboxyl Functional Groups

(a) Flow Through Procedure

The same preferred procedure as that described in the general method of Example 5(a) was employed to prepare a 25 mm diameter DCC activated membrane disc using the controlled surface property, hydrophilic, microporous, skinless, nylon 66 polyamide membrane material having carboxyl functional group modified surfaces employed in Example 4. In this instance, a 25 ml aliquot of DCC was recirculated continuously through a 0.2 micron pore diameter membrane disc at a flow rate of 7.2 ml/minute/$cm^2$ membrane area for 10 minutes. Thereafter, the disc was rinsed with 25 ml of methylene chloride at a flow rate of 7.2 ml/minute/$cm^2$ membrane area.

(b) Immersion Procedure

The procedure described in the general method of Example 5(b) was employed to prepare three DCC activated membranes, each having a membrane area of 1.3 $cm^2$. The hydrophilic, microporous, skinless, nylon 66 polyamide membrane material employed was the same as the controlled surface property carboxyl functional group modified surface membrane material used in Example 4 and had a pore diameter of 0.2 micron.

EXAMPLE 7, General Method of Preparing Biologically Active Membranes

(a) Flow Through Procedure

Biologically active polyamide membranes of the present invention were prepared as follows. Chemically activated membrane discs prepared as in the general methods of Examples 1 and 5 were rendered biologically active by passing through each membrane disc a solution containing a biologically active substance.

A chemically activated membrane disc was placed in a syringe-type filter holder of an appropriate size and the syringe-type filter holder was placed in communication with a reservoir containing a solution of a biologically active substance by means of silicone tubing and supplied with solution by means of a peristaltic pump. Solutions of biologically active substances had concentrations of 0.1 or 0.2 mg/ml and were prepared in phosphate buffered saline (PBS), pH 7.0 to 7.4. The PBS solution consisted of 10 mM sodium phosphate and 130 mM sodium chloride. Reaction of the biologically active substance with functional groups of the bound residue of the activating agents of the chemically activated membrane was effected by passing through the chemically activated membrane at ambient temperature an aliquot (1.6 ml/cm$^2$ of membrane area) of solution composed of a biologically active substance at a flow rate of 0.1 ml/minute/cm$^2$ membrane area. Excess biologically active material was removed by washing with an aliquot (15.6 ml/cm$^2$ of membrane area) of PBS solution at a flow rate of 0.5 ml/minute/cm$^2$ membrane area.

(b) Immersion Procedure

Chemically activated membrane discs, prepared according to the general methods of Examples 1 and 5 were placed in separate sealable bags. Solutions of the biologically active material were prepared in PBS, pH 7.0 to 7.4. The biologically active material (0.4 ml/cm$^2$ of membrane area) was placed in each bag, the bags sealed, and reaction allowed to proceed with the chemically active membrane for a period of 2 hours with agitation at 4 degrees C. After reaction, excess solution of biologically active material was removed and the membrane placed in a second clean plastic bag and washed successively with 3 portions of PBS (2.5 ml/cm$^2$ membrane area) after sealing for 15 minutes per wash with agitation at ambient temperature.

EXAMPLE 8, General Method of Attaching Ligands To Biologically Active Membranes

Chemically activated membrane discs were prepared according to the general methods of Examples 1 and 5 and were biologically activated by immobilizing biologically active materials according to the procedures described in the general method of Example 7. A biospecific ligand was reacted with the biologically active membrane discs by first placing the membrane discs in syringe-type filter holders which were placed in fluid communication with a reservoir by means of silicone tubing. A peristaltic pump was employed to transfer the solution of biospecific ligand to the membrane discs. A 5 ml aliquot (7.8 ml/cm$^2$ of membrane area) of PBS solution, pH 7.0 to 7.4, was introduced to the system and passed through the membrane disc at a flow rate of 2.5 ml/minute/cm$^2$ membrane area at ambient temperature. Potential non-specific binding sites on the biologically activated membrane were blocked in order to avoid any non-specific binding of the ligand to the membrane by passing a solution of a blocking agent (1.6 ml/cm$^2$ of membrane area) of either fetal calf serum (FCS) or 10 percent bovine serum albumin (BSA) through the membrane at a flow rate of 0.5 ml/minute./cm$^2$ membrane area. Excess blocking agent was removed by washing with 15.6 ml/cm$^2$ membrane area of PBS solution at a flow rate of 0.5 ml/minute/cm$^2$ membrane area at ambient temperature. Formation of a biospecific complex between the biologically active material bound to the chemically activated membrane and the ligand in solution was accomplished by passing 1.6 ml/cm$^2$ membrane area of the ligand solution at a flow rate of 0.1 ml/minute/cm$^2$ membrane area through the biologically active membrane at ambient temperature. The biochemically specific ligand was bound to the immobilized biologically active material or acceptor molecule, forming a biospecific complex, as the solution was passed through the membrane. Excess ligand and other solutes were washed from the membrane by flushing with with an aliquot of PBS (15.6 ml/cm$^2$ of membrane area) at a flow rate of 2.5 ml/minute/cm$^2$ membrane area.

EXAMPLE 9, Preparation Of Biologically Active Membranes Using Nylon 66 Membranes and Nylon 66 Membranes Having Controlled Surface Properties (a) Preparation Of Biologically Active Membranes Using Nylon 66 Membranes And Nylon 66 Membranes Having Controlled Surface Properties Characterized By Carboxyl Functional Groups:

Nylon 66 membranes (ULTIPOR N$_{66}$ obtained from Pall Corporation) as described in Example 2 were chemically activated with T-s-T according to Example 2(b). Nylon 66 membranes having controlled surface properties characterized by carboxyl functional groups (CARBOXYDYNE obtained from Pall Corporation) as described in Example 4 were chemically activated with T-s-T according to Example 4(b). Polyclonal rabbit anti-mouse IgG immunoglobulin (RAM) obtained from commercial sources was immobilized on T-s-T activated CARBOXYDYNE (0.2 micron pore diameter), T-s-T activated ULTIPOR N$_{66}$ (0.2 micron pore diameter), chemically unactivated CARBOXYDYNE (0.2 micron pore diameter) and chemically unactivated ULTIPOR N$_{66}$M (0.2 micron pore diameter). Two 13 mm diameter membrane discs of each type listed above were each sealed in separate plastic bags, each containing 0.5 ml of a RAM solution in PBS composed of 0.1 mg/ml RAM and $10^5$ cpm/ml $^{125}$I-labelled RAM, both also obtained from commercial sources. Reaction of chemically activated and unactivated membrane discs with antibody was performed according to the general procedure of Example 7(b) for a period of 2 hours at 4 degrees C.

Excess unadsorbed RAM was removed by washing each membrane disc 3 times with 5 ml aliquots of PBS solution for a period of 15 minutes per wash at 4 degrees C. The amount of antibody initially bound to each membrane disc was then determined by radioactive counting.

After radioactive counting, the membranes were placed in filter holders. The membranes were then further washed with 5 ml of the buffer PBS and thereafter successively with 5 ml portions of dissociating agents, 0.1 percent Triton X-100 in PBS, 1 percent sodium dodecyl sulfate (SDS), and 8M urea, at a flow rate of 0.1 ml/minute/cm$^2$ membrane area. This combination of dissociating agents was chosen in order to strip non-covalently bound antibody from the membrane. The amount of antibody remaining on the membrane after each was determined by radioactive counting. Results are shown in Table 2 below.

TABLE 2

BOUND ANTIBODY ($\mu g/cm^2$ MEMBRANE AREA) REMAINING AFTER EACH WASH

| Membrane | Wash Solution | | | |
|---|---|---|---|---|
| | PBS | Triton X-100 | SDS | Urea |
| Activated CARBOXYDYNE | 17.7 | 15.4 | 14.4 | 13.9 |
| Activated ULTIPOR $N_{66}$ | 15.5 | 12.3 | 10.0 | 9.2 |
| Unactivated CARBOXYDYNE | 17.0 | 1.7 | 0 | 0 |
| Unactivated ULTIPOR $N_{66}$ | 18.7 | 1.0 | 0 | 0 |

T-s-T activated CARBOXYDYNE retained 79 percent of the initially bound antibody after treatment with the dissociating agents listed above, while T-s-T activated ULTIPOR $N_{66}$ retained 59 percent of initially bound antibody after treatment with the dissociating agents. Antibody binding to unactivated CARBOXYDYNE and unactivated ULTIPOR $N_{66}$ membranes were found to be completely reversible by treatment with the detergents Triton X-100 and SDS. The resistance to dissociation of activated membrane-bound antibody represents demonstrable evidence of permanent binding of the RAM antibody molecules to the activated membrane surface, particularly to the T-s-T activated nylon 66 polyamide membrane having controlled surface properties characterized by carboxyl functional groups (CARBOXYDYNE) of the present invention.

(b) Preparation Of Biologically Active Membranes Using Nylon 66 Membranes Having Controlled Surface Properties Nylon 66 membranes having controlled surface properties characterized by amine functional groups (AMINODYNE obtained from Pall Corporation) and described in Example 3 were chemically activated with T-s-T according to Example 1(b). Nylon 66 membranes having controlled surface properties characterized by carboxyl functional groups (CARBOXYDYNE obtained from Pall Corporation) as described in Example 4 were chemically activated with T-s-T according to Example 1(b),.

Polyclonal rabbit anti-mouse IgG immunoglobulin was immobilized on T-s-T activated CARBOXYDYNE (0.1 micron pore diameter), T-s-T activated AMINODYNE (0.1 micron pore diameter), unactivated CARBOXYDYNE (0.1 micron pore diameter) and unactivated AMINODYNE (0.1 micron pore diameter). Two 13 mm diameter membrane discs of each type listed above were each sealed in separate plastic bags containing 0.5 ml of RAM solution in PBS having a concentration of 0.1 mg/ml RAM and $10^5$ cpm/ml of $^{125}$I-labelled RAM, both obtained from commercial sources. Reaction of chemically activated and unactivated discs with antibody was performed according to the general method described in Example 7(b) for a period of 2 hours at 4 degrees C.

Excess unreacted antibody was removed by washing each membrane disc 3 times with 5 ml portions of PBS solution for a period of 15 minutes per wash at 4 degrees C. The amount of antibody initially bound to each membrane was then determined by radioactive counting.

After radioactive counting, the membranes were placed in plastic bags and were washed twice with 5 ml of 1 percent sodium dodecyl sulfate (SDS) per membrane, 15 minutes per wash at 4 degrees C to remove non-covalently attached antibody. The amount of antibody remaining on the membranes after SDS washing was then determined again by radioactive counting. The results are presented below in Table 3.

TABLE 3

| Membrane | BOUND ANTIBODY ($\mu g/cm^2$) REMAINING AFTER WASH | |
|---|---|---|
| | PBS | SDS |
| Activated CARBOXYDYNE | 14.6 | 13.2 |
| Activated AMINODYNE | 16.2 | 12.2 |
| Unactivated CARBOXYDYNE | 14.9 | 1.8 |
| Unactivated AMINODYNE | 13.5 | 3.7 |

The T-s-T activated 0.1 micron pore diameter CARBOXYDYNE membrane of the present invention retained the most antibody after SDS wash at 13.2 micrograms/$cm^2$ membrane area. T-s-T activated CARBOXYDYNE and T-s-T activated AMINODYNE each retained 90.4 and 75.3 percent of initially bound antibody, respectively, after the stringent SDS wash, whereas the same membrane materials in unactivated form retained only 12.1 and 27.4 percent of initial bound antibody, respectively, when treated under the same stringent wash conditions. Thus, the T-s-T activation procedure employed on the controlled surface property membranes effected almost a three-fold enhancement of non-dissociable binding of antibody to the AMINODYNE membrane surface and over a seven-fold enhancement of non-dissociable binding of antibody to the CARBOXYDYNE membrane surface.

EXAMPLE 10, Preparation Of A Biologically Active Membrane By Immobilization of Polyclonal Rabbit Anti-Mouse IgG On N, N'-Dicyclohexylcarbodiimide-Activated Membranes Two N, N'-dicyclohexylcarbodiimide (DCC) activated nylon membranes having controlled surface properties characterized by carboxyl functional group modified surfaces (CARBOXYDYNE) were prepared by the method and using the material of Example 6(a). These activated membranes and 2 unactivated membranes formed from the same membrane material, each having a surface area of 1.3 $cm^2$, were placed in separate plastic bags containing 0.5 ml of polyclonal rabbit anti-mouse IgG (RAM) solution (0.4 ml/$cm^2$ of membrane area). The RAM solution, prepared in PBS, had a concentration of 0.2 mg/ml unlabelled RAM and $1.2 \times 10^5$ cpm/ml of $^{125}$I-labelled RAM. The plastic bags were sealed and the procedure for binding the biologically material described in the general method of Example 7(b) was employed. After reaction of the membranes with RAM solution, each of the membranes was washed successively 3 times with 3.3 ml portions of a PBS solution, 3 times with 3.3. ml portions of PBS solution containing 0.1 percent Triton X-100, and finally once with 3.3 ml of PBS. The washes were performed at 4 degrees C and were each of 15 minutes duration.

The amount of RAM antibody bound to the membranes was determined by radioactive counting. The DCC activated and unactivated membranes bound an average of 20 micrograms/$cm^2$ membrane area and 6 micrograms/$cm^2$ membrane area of RAM, respectively. The DCC activation procedure employed with the carboxyl functional group surface modified nylon 66 membranes of the present invention, therefore, provided over a three-fold increase in the amount of biologically active material capable of being immobilized on the membrane surface as compared to the unactivated membrane.

EXAMPLE 11, Preparation Of A Biologically Active Membrane By Immobilization Of Polyclonal Rabbit Anti-Mouse IgG On A T-s-T Activated Nylon 66 Membrane Two T-s-T activated 13 mm diameter membrane discs were prepared using the carboxyl functional group controlled surface membrane material (CARBOXYDYNE 0.2 micron pore diameter) of Example 4(a) and the activation procedure of Example 1(b) and two unactivated membrane discs of the same membrane material were biologically activated by separately reacting all of the discs with a solution containing rabbit anti-mouse IgG (RAM antibody) as in the general method of Example 7(a). Specifically, a solution containing 0.1 mg/ml RAM and $10^5$ cpm/ml $^{125}$I-labelled RAM, both obtained from commercial suppliers, was prepared in PBS solution. One ml aliquots of the RAM solution were passed through each membrane disc. Unreacted RAM was removed from the discs by passing 10 ml aliquots of PBS solution through each membrane disc. Each membrane disc was then flushed with a 10 ml aliquot of 1 percent SDS at a flow rate of 0.5 ml/minute/cm$^2$ membrane area to remove the non-covalently bound antibody. The extent of RAM immobilization and retention was measured by radioactive counting of each membrane disc after each wash treatment.

After the SDS wash, T-s-T activated membrane discs bound an average of 39.6 mg/cm$^2$ membrane area of RAM while unactivated membrane discs bound an average of only 3.9 mg/cm$^2$ membrane area of RAM. The enhanced binding of RAM to T-s-T activated membranes represents a ten-fold increase in the amount of nondissociable antibody binding over unactivated membranes. The significant increase of antibody retention results from antibody permanently immobilized on the T-s-T activated membrane surfaces versus adsorptive SDS dissociable binding of RAM to the membrane itself.

EXAMPLE 12, Preparation Of A Rabbit IgG Biologically Active Membrane With Subsequent Attachment Of Goat Anti-Rabbit IgG (a) Immobilization Of Antigen:

Polyclonal rabbit IgG (antigen) was immobilized according to the general method of Example 7(b) on T-s-T activated membrane discs as described in Example 4(b). T-s-T activated membrane discs were sealed in separate plastic bags, each with 0.5 ml aliquots of a solution in PBS of rabbit IgG containing 0.2 mg/ml rabbit IgG obtained from commercial sources. The antibody was reacted with the membrane discs according to Example 7(b) for a period of 2 hours at 4 degrees C. Unreacted antibody was then removed by washing the membrane discs 3 times with a PBS solution.

(b) Attachment Of Goat Anti-Rabbit IgG To Immobilized Rabbit IgG

Polyclonal goat anti-rabbit IgG (GARG, antibody) which reacts with rabbit IgG to form a reversible, biospecific immune complex was obtained from commercial sources and reacted with the biologically active membrane described in Example 12(a) to form a biospecific immune complex according to the general procedure described in Example 8. As a means of determining the extent of binding attributable to the biologically active material immobilized on the membrane, a chemically activated membrane disc was used as a control for comparison with the biologically active membrane disc. Specifically, a 13 mm diameter T-s-T activated control disc (without rabbit IgG) and the rabbit IgG biologically active membrane discs were pre-treated to block non-specific protein binding sites by passing 1 ml of fetal calf serum (FCS) through each membrane disc at a flow rate of 0.5 ml/minute/cm$^2$ membrane area. A GARG solution in PBS, containing 0.2 mg/ml of a stabilizing agent, bovine serum albumin (BSA), 1 microgram/ml of commercially supplied GARG and $2 \times 10^5$ cpm/ml of commercially supplied $^{125}$I-labelled GARG was then passed through the membrane to form the biospecific complex. Attachment was effected by passing 1 ml of the GARG solution through each membrane disc in the manner described in the general method of Example 8. Radioactive counting of each of the discs indicated the chemically activated control disc (without rabbit IgG) bound only 9 percent of the available GARG while the rabbit IgG biologically active membrane disc bound 40 percent of the available GARG.

The results indicated that binding of a ligand is improved almost 450 percent by use of an appropriate biologically active membrane prepared by immobilization of a specific biologically active substance to a chemically activated membrane of the present invention as compared to binding on a membrane which has merely been chemically activated.

EXAMPLE 13, Preparation Of A Biologically Active Monoclonal IgM Antibody-Immobilized Membrane With Subsequent Attachment Of Antigen (a) Immobilization Of Monoclonal Anti-Hepatitis B Antibody On A Trichloro-s-Triazine Activated Membrane The monoclonal antibody 5D$_3$IgM anti-hepatitis B (anti-HBs), derived from the double cloned cell line designated 5D$_3$ and characterized by its specificity for binding hepatitis B surface antigen (HBsAg), was immobilized on polyamide membranes of the type described in Example 4 which were T-s-T activated by a modification of the general method described in Example 1(b). These T-s-T activated membranes were prepared as follows. Membrane discs (25 m the membrane material of Example 4 were baked for one hour at 80 degrees C. The membrane discs were then placed in a 500 ml Erlenmeyer flask and were prereacted with 10 ml of diisopropylethylamine in 110 ml dioxane for 30 minutes with continuous agitation at 50 degrees C. An aliquot of 1 M T-s-T solution in dioxane (20 ml) was then added to the flask. Membrane discs were allowed to react with T-s-T for 1 hour at 50 degrees C before the solution was decanted. Unreacted T-s-T and diisopropylethylamine were removed by washing membranes twice with 100 ml aliquots of dioxane, 5 minutes per wash, at ambient temperature. A 100 ml solution containing 2 M aniline in dioxane was then added to the flask. Membranes were allowed to react with aniline for 30 minutes at ambient temperature. The aniline was then decanted and the unreacted reagent removed by washing membranes twice each with 100 ml aliquots of dioxane, 70 percent (v/v) aqueous dioxane, twice with 30 percent (v/v) aqueous dioxane, and 5 times with distilled water, 5 minutes per wash. The T-s-T activated membranes were blotted dry, air dried for approximately 15 minutes, and then stored in a desiccator under vacuum until required for use.

Two of the above-described 25 mm diameter T-s-T activated membrane discs having 4.9 cm$^2$ membrane area were sealed in separate plastic bags containing 2.0 ml of a solution in PBS of 5D$_3$ IgM anti-HBs antibody having a concentration of 0.2 mg/ml of unlabelled antibody and 10$^5$ cpm/ml of $^{125}$I-5D$_3$ IgM anti-HBs, both antibodies obtained from a commerical supplier. Reaction of chemically activated membrane discs with monoclonal antibody was performed according to the general method of Example 7(b) for a period of 2 hours at 4 degrees C.

Unreacted antibody was removed by washing each membrane disc with 12 ml of PBS solution containing 0.1 percent Triton X-100 for a period of 30 minutes. The membrane discs were thereafter washed in the above solution for 2 consecutive days. After washing, the discs contained an average amount of antibody equal to 45 micrograms of 5D$_3$ IgM anti-HBs/cm$^2$ of membrane area as determined by radioactive counting in a gamma counter.

(b) Attachment Of Hepatitis B Surface Antigen (HBsAg) To Membrane Immobilized 5D$_3$ IgM Anti-HBs Monoclonal Antibody A biologically activated membrane having the monoclonal antibody 5D$_3$ IgM anti-HBs bound thereto was prepared as described in Example 13(a). Specifically, a 13 mm diameter T-s-T activated membrane disc of the polyamide membrane material of Example 4 was employed and was prepared according to the method described in Example 13(a) by sealing the membrane in a plastic bag containing 0.5 ml of a solution in PBS of 5D$_3$ IgM anti-HBs having a concentration of 0.2 mg/ml of 5D$_3$ IgM anti-HBs from a commercial source. The antibody was reacted with the membrane according to the general method of Example 7(b) for a period of two hours at 4 degrees C. Unreacted antibody was then removed by washing the membranes twice with a PBS solution containing 0.1 percent Triton X-100 for a period of 15 minutes per wash. Subsequently, the membranes were washed once in PBS solution for 15 minutes and then stored in PBS solution at 4 degrees C for a period of 4 days. Reaction of the antigen HBsAg with the 5D$_3$ IgM anti-HBs biologically active membrane was effected by treating the biologically active membrane disc in the manner described in Example 8 with a 13 mm diameter T-s-T activated membrane disc, activated as per Example 13(a), included as a control.

Through each of the membrane discs was passed 1 ml of FCS at a flow rate of 0.5 ml/min/cm$^2$ membrane area to block any non-specific binding sites on the membrane discs. An HBsAg solution containing 27 ng/ml of "ayw" subtype and 36 ng/ml of "adw" subtype of commercially available HBsAg was diluted with FCS to a final concentration of 2.33 ng/ml. A portion of this HBsAg solution was set aside for subsequent evaluation by a radioimmunoassay (RIA) and 1 ml aliquots of the remaining antigen solution were then passed through each of the membrane discs at a flow rate of 0.1 ml/min/cm$^2$ membrane area. Removal of HBsAg from serum was evaluated by performing an RIA on the influent sample and the filtrates of the two membrane discs. The membrane disc which was biologically activated with 5D$_3$ IgM anti-HBs reduced the concentraton of HBsAg in serum by 43 percent from an initial concentration of 2.33 ng/ml to a concentration of 1.33 ng/ml as a result of the formation of the biospecific complex. Chemically activated membrane discs which did not contain immobilized 5D$_3$ IgM anti-HBs reduced the concentration of the HBsAg in serum by only 7 percent from a value of 2.33 ng/ml to a final concentration of 2.17 ng/ml.

The results indicate that a ligand, such as the antigen in the instant example, may be selectively removed from serum by formation of a biospecific complex, in the present situation an immune complex, with a monoclonal antibody activated membrane. Removal of the antigenic material HBsAg occurred to a significantly greater extent with the biologically active membrane disc than the negligible binding of the antigen which occurred with the chemically activated control disc.

EXAMPLE 14, Preparation Of A Polyclonal Goat Anti-Rabbit IgG Antibody Biologically Active Membrane With Subsequent Attachment And Elution Of Rabbit IgG (Antigen)

(a) Preparation Of A Biologically Active Membrane By Immobilization Of Polyclonal Goat Anti-Rabbit IgG On A Trichloro-s-Triazine Activated Membrane Polyclonal goat anti-rabbit IgG (GARG) was obtained in both $^{125}$I-labelled and unlabelled formed from commercial sources. A solution containing 0.1 mg/ml unlabelled GARG and 1.1×10$^5$ cpm/ml $^{125}$I-labelled GARG was prepared in PBS solution. One ml aliquots of the GARG were passed through and thereby reacted with two T-s-T activated 13 mm diameter membrane discs having carboxyl functional group modified surfaces as described in Example 4(b) and activated according to the method of Example 1(b), following the procedure of Example 7(a). Two unactivated membrane discs of the same membrane material were also treated according to the general method described in Example 7(a). At completion of the reaction, each membrane disc was washed with 10 ml of PBS solution to remove unadsorbed and unreacted GARG. The amount of GARG bound to each membrane disc was then determined by radioactive counting in a gamma counter. The counts disclosed that unactivated membrane discs bound an average of 50.6 micrograms/cm$^2$ membrane area of GARG while T-s-T activated membrane discs bound an average 81.3 micrograms/cm$^2$ membrane area of GARG.

Each membrane disc was washed further with 10 ml of 1 percent sodium dodecyl sulfate (SDS) at a flow rate of 0.5 ml/minute/cm$^2$ membrane area to dissociate and remove weak, non-covalently linked antibody. Following SDS treatment, unactivated membrane discs retained an average of only 26 percent of the initial bound GARG or 13.3 micrograms/cm$^2$ membrane area while the T-s-T activated membrane discs retained an average of 83 percent of the initial bound GARG or 67.3 micrograms/cm$^2$ membrane area of GARG. T-s-T activated membrane discs retained 80 percent more antibody than unactivated membrane discs composed of the same membrane material. Thus, the non-dissociable nature of the bonding between antibody and T-s-T activated membranes is shown by the integrity of these bonds when exposed to stringent dissociative conditions.

(b) Attachment Of Rabbit IgG To A Membrane Having Goat Anti-Rabbit IgG Immobilized Thereon T-s-T activated nylon 66 membranes having controlled surface properties characterized by carboxyl functional group modified surfaces as described in Example 4(a) were activated according to the general method of Example 1(b). These membrane discs, each having a diameter of 13 mm and a membrane area of 1.3 cm$^2$ were then biologically activated with goat antirabbit IgG (GARG) as described in Example 14(a). Thus, 1 ml portions of a GARG solution in PBS containing 100 micrograms/ml GARG obtained from commercial sources were passed through each of two chemically active membrane discs at a flow rate of 0.1 ml/minute/cm$^2$ membrane area. These GARG biologically active membrane discs were then utilized to remove rabbit IgG from a solution to form a biospecific complex, in this instance an immune complex. The reaction of the ligand, rabbit IgG, with the immobilized GARG was effected by treating the GARG biologically active membrane disc in the manner described in the general method of Example 8. Potential non-specific binding sites on the membrane were blocked by passing a 1 ml aliquot of a bovine serum albumin (BSA) solution containing 10 percent (w/v) BSA in PBS through each biologically active membrane disc at a flow rate of 0.5 ml/minute/cm$^2$ membrane area. Excess BSA was then removed from the membrane discs by passing 10 ml of PBS solution through each membrane disc at a flow rate of 0.5 ml/minute/cm$^2$ membrane area. Thereafter, a 1 ml portion of a solution containing 100 micrograms/ml rabbit IgG and $2.8 \times 10^5$ cpm/ml of $^{125}$I-labelled rabbit IgG (both obtained commercially) was passed through each GARG biologically active membrane disc at a flow rate of 0.1 ml/minute/cm$^2$ membrane area. Unreactived rabbit IgG was removed from the membrane discs by passing 10 ml of a PBS solution through the membrane discs. The amount of rabbit IgG attached to the biologically active membrane was determined to be 27.1 micrograms/cm$^2$ membrane area by radioactive counting.

(c) Recovery Of Rabbit IgG From A Rabbit IgG-Bound Goat Anti-Rabbit IgG Biologically Active Membrane:

Rabbit IgG bound to the goat anti-rabbit IgG (GARG) biologically active membrane of Example 14(b) was recovered by passing 10 ml of 50 mM glycine. HCl, pH of 2.2, buffered with PBS, through the membrane at a flow rate of 0.5 ml/minute/cm$^2$ membrane area. Subsequent counting of the eluate and the membrane disclosed that 30 percent of the attached rabbit IgG was released from the GARG biologically active membrane disc as a result of this treatment.

EXAMPLE 15, Preparation Of A Protein A Biologically Active Membrane With Attachment And Subsequent Elution Of IgG Immunoglobulin

(a) Preparation Of A Biologically Active Membrane By Immobilization Of Protein A On a T-s-T Activated Membrane:

Protein A, isolated from *Staphylococcus aureus*, Cowan strain, and consisting of a single polypeptide chain having a molecular weight of 42,000 was immobilized on 2 T-s-T activated 13 mm diameter membrane discs, prepared as described in Example 4(b) according to the procedure described in the general method of Example 7(b). Each chemically activated membrane disc was placed in a separate plastic bag containing 0.5 ml of a solution in PBS composed of 0.2 mg/ml unlabelled Protein A and $1.3 \times 10^5$ cpm/ml of $^{125}$I-labelled Protein A, both obtained commercially. The bags were sealed and the membrane discs were reacted with the Protein A solution for 2 hours at 4 degrees C, washed 3 times with 3.3 ml of PBS solution as described in Example 7(b) and counted in a gamma counter. Protein A was bound to the extent of 54.6 and 51.5 micrograms/cm$^2$ membrane area, respectively, for each of the T-s-T activated membrane discs.

(b) Attachment Of Rabbit IgG To A Membrane Bioloqically Activated With Protein A Biologically active membrane discs in which Protein A was bound to the membrane through T-s-T derived linkages were prepared as described above in Example 15(a). Two of the discs so prepared, each having a diameter of 13 mm, were reacted with a solution containing rabbit IgG to enable formation of a biospecific complex in which rabbit IgG is bound to the Protein A immobilized on the membrane through the Fc region of the IgG molecule. The procedure described in the general method of Example 8 was employed to form the biospecific complex. Specifically, a 2 ml aliquot of rabbit IgG solution in PBS, containing 0.2 mg/ml rabbit IgG and $10^5$ cpm/ml of $^{125}$I-labelled rabbit IgG, both obtained commercially, was recirculated through each Protein A biologically active membrane disc for a total of 2 to 4 passes at a flow rate of 0.1 ml/minute/cm$^2$ membrane area. Based on the total counts of rabbit IgG available to each Protein A biologically active membrane, 96.7 and 70.2 micrograms/cm$^2$ membrane area of rabbit IgG were bound to each of the discs, respectively.

(c) Recovery of Rabbit IgG From A Protein A Biologically Active Membrane Having Rabbit IgG Bound Thereto Rabbit IgG was eluted from the biospecific complex formed with two of the Protein A biologically active membranes prepared according to the method of Example 7(b). This was accomplished by placing each of the membrane discs in a syringe-type filter holder and passing 10 ml of an eluting agent, 8 M urea, through each membrane at a flow rate of 0.5 ml/minute/cm$^2$ membrane area. Counting of the eluates indicated that 23 micrograms of a total of 62 micrograms rabbit IgG bound to 1 disc were recovered and 17 micrograms of a total of 45 micrograms rabbit IgG bound to a second disc were recovered. This corresponds to recoveries of 37 and 38 percent, respectively.

We claim:

1. A method of preparing a biologically active membrane having a large surface area comprising the steps of:

reacting a hydrophilic, microporous, skinless polyamide membrane with an activating agent to form a chemically activated membrane, and reacting said chemically activated membrane with an acceptor molecule to form a biologically active membrane, said acceptor molecule being a member selected from the group consisting of a monoclonal antibody, a polyclonal antibody, an antigenic substance, a glycoprotein, Protein A, a lectin, a carbohydrate, an enzyme substrate, a cofactor, an inhibitor, a hormone, an IgG class of immunoglobulin, a carrier protein, a receptor, heparin, a coagulation factor, and a histone.

2. The method of claim 1 wherein said polyamide membrane comprises polyhexamethylene adipamide.

3. The method of claim 2 wherein said membrane is formed from a material modified to include controlled surface properties.

4. The method of claim 2 wherein said modified polyamide membrane includes a high concentration of carboxyl moieties.

5. The method of claim 2 wherein said activating agent includes at least one functional group capable of reacting with moieties on the surface of said polyamide membrane to form an activated membrane having a functional group capable of reacting with said acceptor molecule.

6. The method of claim 2 wherein said acceptor molecule is a monoclonal antibody.

7. The method of claim 2 wherein said activating agent comprises trichloro-s-triazine.

8. The method of claim 2 wherein said activating agent comprises N,N'-dicyclohexylcarbodiimide.

9. The method of claim 2 wherein a substrate is embedded in said membrane.

10. A method for preparing a biologically active membrane having a large surface area comprising the steps of:
reacting a hydrophilic, microporous, skinless, polyamide membrane with an activating agent to form a chemically activated membrane wherein said activating agent is either trichloro-s-triazine or N,N'-dicyclohexylcarbodiimide, and
reacting said chemically activated membrane with an acceptor molecule to form a biologically active membrane.

11. The method of claim 10 wherein said acceptor molecule is capable of reacting with a ligand to form a stable biospecific complex.

12. The method of claim 10 wherein said acceptor molecule is a proteinaceous substance.

13. The method of claim 11 wherein said acceptor molecule is a member selected from the group consisting of a monoclonal antibody, a polyclonal antibody, an antigenic substance, a glycoprotein, Protein A, a lectin, a carbohydrate, an enzyme substrate, a cofactor, an inhibitor, a hormone, an IgG class of immunoglobulin, a carrier protein, a receptor, heparin, a coagulation factor, and a histone.

14. A biologically active membrane having a large surface area comprising an acceptor molecule selected from the group consisting of a monoclonal antibody, a polyclonal antibody, an antigenic substance, a glycoprotein, Protein A, a lectin, a carbohydrate, an enzyme substrate, a cofactor, an inhibitor, a hormone, an IgG class of immunoglobulin, a carrier protein, a receptor, heparin, a coagulation factor, and a histone covalently bound to a hydrophilic, microporous, skinless polyamide membrane.

15. The biologically active membrane of claim 14 wherein said polyamide membrane comprises polyhexamethylene adipamide.

16. The biologically active membrane of claim 15 wherein said polyamide membrane has a methylene $CH_2$:amide NHCO ratio of from about 5:1 to about 7:1.

17. The biologically active membrane of claim 15 wherein said polyamide membrane is modified to include controlled surface properties.

18. The biologically active membrane of claim 17 wherein said controlled surface properties include a high concentration of carboxyl moieties.

19. The biologically active membrane of claim 15 wherein a residue of an activating agent covalently links said acceptor molecule to said hydrophilic, microporous, skinless polyamide membrane.

20. The biologically active membrane of claim 19 wherein said residue of an activating agent comprises a residue of trichloro-s-triazine.

21. A biologically active membrane having a large surface area comprising an acceptor molecule covalently bound to a hydrophilic, microporous, skinless, polyamide membrane through a residue of trichloro-s-triazine.

22. The biologically active membrane of claim 21 wherein said acceptor molecule is capable of reacting with a ligand to form a stable biospecific complex.

23. The biologically active membrane of claim 21 wherein said biologically active material is a proteinaceous substance.

24. The biologically active membrane of claim 21 wherein said acceptor molecule is a member selected from the group consisting of a monoclonal antibody, a polyclonal antibody, an antigenic substance, a glycoprotein, Protein A, a lectin, a carbohydrate, an enzyme substrate, a cofactor, an inhibitor, a hormone, an IgG class of immunoglobulin, a carrier protein, a receptor, heparin, and a coagulation factor.

25. The biologically active membrane of claim 21 wherein said acceptor molecule is a monoclonal antibody.

26. The biologically active membrane of claim 15 wherein a substrate is embedded in said membrane.

27. A filter element comprising the biologically active membrane of claim 26 wherein said membrane is positioned intermediate porous support sheets forming thereby a membrane element and said membrane element is arranged in a tubular corrugated configuration having axially extending pleats, said tubular configured membrane element being placed intermediate a pair of concentric, cylindrical, rigid, perforated tubes, the ends of said tubular configured membrane element and said concentric cylindrical tubes being closed off with end caps forming a fluid-tight seal between said tubular configured membrane element and said concentric perforated tubes.

28. A method for recovering a ligand from a solution including passing a ligand solution through a biologically active membrane comprising an acceptor molecule selected from the group consisting of a monoclonal antibody, a polyclonal anitbody, an antigenic substance, a glycoprotein, Protein A, a lectin, a carbohydrate, an enzyme substrate, a cofactor, an inhibitor, a hormone, an IgG class of immunoglobulins, a carrier protein, a receptor, heparin, a coagulation factor, and a histone covalently bound to a hydrophilic, microporous, skinless polyamide membrane and binding said ligand to said biologically active membrane.

29. The method of claim 28 wherein said polyamide membrane comprises polyhexamethylene adipamide.

30. The method of claim 29 wherein said polyamide membrane is formed from a material modified to include controlled surface properties.

31. The method of claim 30 wherein said polyamide membrane includes a high concentration of carboxyl moieties.

32. The method of claim 29 wherein a substrate is embedded in said polyamide membrane.

33. The method of claim 29 wherein said ligand is a proteinaceous substance.

34. The method of claim 29 wherein said ligand is a member of a group consisting of an antigenic substance, a monoclonal antibody, a polyclonal antibody, a lectin, a glycoprotein, a carbohydrate, Protein A, an enzyme, a carrier protein, a receptor, a hormone, a coagulation factor, heparin, a nucleic acid, and a polynucleotide.

35. A method for recovering a ligand from a solution including passing a ligand solution through a biologically active membrane comprising an acceptor molecule covalently bound to a hydrophilic, microporous, skinless, polyamide membrane through a residue of trichloro-s-triazine and binding said ligand to said biologically active membrane.

36. The method of claim 35 wherein said acceptor molecule is a member selected from the group consisting of a monoclonal antibody, a polyclonal antibody, an antigenic substance, a glycoprotein, Protein A, a lectin, a carbohydrate, an enzyme substrate, a cofactor, an inhibitor, a hormone, an IgG class of immunoglobulins, a carrier protein, a receptor, heparin, a coagulation factor, and a histone.

37. The method of claim 35 wherein said acceptor molecule is a proteinaceous substance.

38. The method of claim 36 wherein said acceptor molecule is a monoclonal antibody.

39. The method of claim 29 wherein said acceptor molecule is chemically bound to said polyamide membrane through a residue of an activating agent.

40. The method of claim 39 wherein said activating agent comprises trichloro-s-triazine.

41. The method of claim 29 wherein the bound ligand is eluted from said biologically active membrane.

42. The method of claim 29 wherein a substrate is embedded in said membrane.

43. The method of claim 42 wherein said membrane is positioned intermediate between porous support sheets, forming thereby a membrane element, and said membrane element is arranged in a tubularical corrugated configuration having axially extending pleats, said tubular configured membrane element being placed intermediate a pair of concentric, cylindrical, rigid, perforated tubes, the ends of said concentric, cylindrical tubes and said tubular configured membrane element being closed of with end caps to form a fluid-tight seal between said tubular configured membrane element and said concentric perforated tubes.

44. A method for preparing a chemically activated membrane comprising reacting a hydrophilic, microporous, skinless polyamide membrane with an activating agent derived from trichloro-s-triazine or N, N'-dicyclohexylcarbodiimide to form a chemically activated membrane.

45. The method of claim 44 wherein said polyamide membrane comprises polyhexamethylene adipamide.

46. The method of claim 45 wherein said membrane is formed from a material modified to include controlled surface properties.

47. The method of claim 46 wherein said modified polyamide membrane includes a high concentration of carboxyl moieties.

48. The method of claim 45 wherein said polyamide membrane has a methylene CH$_2$:amide NHCO ratio of from about 5:1 to about 7:1.

49. The method of claim 45 wherein said polyamide membrane is modified to include controlled surface properties.

50. The method of claim 49 wherein said controlled surface properties include a high concentration of carboxyl moieties.

51. The method of claim 45 wherein a substrate is embedded in said membrane.

52. The method of claim 51 wherein said membrane is positioned intermediate porous support sheets, forming thereby a membrane element, and said membrane element is arranged in a tubular corrugated configuration having axially extending pleats, said tubular configured membrane element being placed intermediate a pair of concentric, cylindrical, rigid, perforated tubes, the ends of said tubular configured membrane element and said concentric, cylindrical tubes being closed off with end caps to form a fluid-tight seal between said tubular configured membrane element and said concentric perforated tubes.

53. A chemically active membrane having a large surface area comprising a hydrophilic, microporous, skinless, polyamide membrane chemically bound to a residue of an activating agent, which residue is derived from trichloro-s-triazine or N, N' dicyclohexylcarbodiimide and is capable of reacting with a biologically active material.

54. The chemically active membrane of claim 53 wherein said polyamide membrane comprises polyhexamethylene adipamide.

55. The chemically active membrane of claim 54 wherein said polyamide membrane has a methylene CH$_2$:amide NHCO ratio of about 5:1 to about 7:1.

56. The chemically active membrane of claim 54 wherein said polyamide membrane is modified to include controlled surface properties.

57. The chemically active membrane of claim 56 wherein said polyamide membrane includes a high concentration of carboxyl moieties at the surface of said membrane.

58. The chemically active membrane of claim 54 wherein said residue is derived from trichloro-s-triazine.

59. The chemically active membrane of claim 54 wherein said residue is derived from N,N'-dicyclohexylcarbodiimide.

60. The chemically active membrane of claim 54 wherein a substrate is embedded in said membrane.

61. A filter element comprising the chemically active membrane of claim 60 wherein said membrane is positioned intermediate porous support sheets, forming thereby a membrane element, and said membrane element is arranged in a tubular corrugated configuration having axially extending pleats, said tubular configured membrane element being placed intermediate a pair of concentric, cylindrical, rigid, perforated tubes, the open ends of said tubular configured membrane element and said concentric, cylindrical tubes being closed off with end caps forming a fluid-tight seal between said tubular configured membrane element and said concentric, cylindrical tubes.

* * * * *